(12) United States Patent
Zhu et al.

(10) Patent No.: US 12,329,384 B2
(45) Date of Patent: Jun. 17, 2025

(54) SURGICAL STAPLER

(71) Applicant: ANHUI BAINUOJIA MEDICAL TECHNOLOGY CO., LTD, Huangshan (CN)

(72) Inventors: Bubing Zhu, Nanjing (CN); Zhen Wang, Nanjing (CN); Huamin Sun, Huai'an (CN); Dongming Li, Changzhou (CN)

(73) Assignee: ANHUI BAINUOJIA MEDICAL TECHNOLOGY CO., LTD, Huangshan (CN)

( * ) Notice: Subject to any disclaimer, the term of this patent is extended or adjusted under 35 U.S.C. 154(b) by 0 days.

(21) Appl. No.: 18/842,412

(22) PCT Filed: Mar. 21, 2023

(86) PCT No.: PCT/CN2023/082657
§ 371 (c)(1),
(2) Date: Aug. 29, 2024

(87) PCT Pub. No.: WO2024/040950
PCT Pub. Date: Feb. 29, 2024

(65) Prior Publication Data
US 2025/0107804 A1    Apr. 3, 2025

(30) Foreign Application Priority Data

Aug. 24, 2022 (CN) .......................... 202211018873.6

(51) Int. Cl.
*A61B 17/072* (2006.01)
*A61B 17/115* (2006.01)
(Continued)

(52) U.S. Cl.
CPC .......... *A61B 17/115* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/07292; A61B 17/115;
(Continued)

(56) References Cited

U.S. PATENT DOCUMENTS 6,716,233 B1 * 4/2004 Whitman ............. A61B 17/115
606/219
10,499,913 B2 * 12/2019 Vendely .................... A61F 2/04
(Continued)

FOREIGN PATENT DOCUMENTS

CN         2531806 Y     1/2003
CN         1203813 C     6/2005
(Continued)

*Primary Examiner* — Scott A Smith
(74) *Attorney, Agent, or Firm* — Bayramoglu Law Offices LLC

(57) ABSTRACT

A surgical stapler includes an anvil and a cartridge that cooperate with each other, a handle, and a connecting tube for connecting the cartridge to the handle. A stent mounting rod is arranged at a front end of the anvil, and a stent for distracting an orifice is movably connected to the stent mounting rod. The stent has a flexible and deformable tubular structure and can distract a lumen of the human orifice after a radial constraint is removed. The stent is coated with an anti-leakage film. An anti-reflux film is further arranged on the stent. The surgical stapler can effectively solve some complications after anastomosis by an existing surgical stapler, and can be widely used in the technical field of medical anastomosis.

7 Claims, 2 Drawing Sheets

(51) Int. Cl.
 *A61B 17/068* (2006.01)
 *A61B 17/29* (2006.01)
 *A61L 31/14* (2006.01)
 *A61L 31/16* (2006.01)

(52) U.S. Cl.
 CPC ... *A61B 17/068* (2013.01); *A61B 2017/07214* (2013.01); *A61B 2017/2927* (2013.01); *A61L 31/146* (2013.01); *A61L 31/16* (2013.01)

(58) Field of Classification Search
 CPC ............ A61B 17/1155; A61B 17/1219; A61B 2017/07214; A61B 2017/07228; A61B 2017/2927; A61L 31/146; A61L 31/16; A61L 31/08
 USPC ..... 227/19, 176.1, 175.1, 175.2; 606/1, 139, 606/219
 See application file for complete search history.

(56) References Cited

U.S. PATENT DOCUMENTS

| | | | |
|---|---|---|---|
| 10,918,388 B2* | 2/2021 | Nativ | A61B 17/07292 |
| 11,129,612 B2* | 9/2021 | Shelton, IV | A61B 17/07292 |
| 2006/0173470 A1* | 8/2006 | Oray | A61B 17/07207 |
| | | | 606/151 |
| 2008/0110961 A1* | 5/2008 | Voegele | A61B 17/115 |
| | | | 606/220 |
| 2008/0132923 A1 | 6/2008 | Fowler et al. | |
| 2009/0043334 A1* | 2/2009 | Bauman | A61B 17/072 |
| | | | 606/214 |
| 2013/0193190 A1 | 8/2013 | Carter et al. | |
| 2014/0358167 A1* | 12/2014 | Armstrong | A61B 17/07292 |
| | | | 227/175.1 |
| 2017/0055994 A1* | 3/2017 | Vendely | A61F 2/04 |

FOREIGN PATENT DOCUMENTS

| | | |
|---|---|---|
| CN | 2712284 Y | 7/2005 |
| CN | 103607975 B | 8/2016 |
| CN | 109044440 A | 12/2018 |
| CN | 109688944 A | 4/2019 |
| CN | 115281764 A | 11/2022 |

\* cited by examiner

SURGICAL STAPLER

CROSS-REFERENCE TO THE RELATED APPLICATIONS

This application is the national phase entry of International Application No. PCT/CN2023/082657, filed on Mar. 21, 2023, which is based upon and claims priority to Chinese Patent Application No. 202211018873.6, filed on Aug. 24, 2022, the entire contents of which are incorporated herein by reference.

TECHNICAL FIELD

The present disclosure relates to the technical field of medical devices, and in particular to a surgical stapler.

BACKGROUND

A stapler as a medical device for replacing manual anastomosis is widely used in surgical anastomosis of digestive tract physiological tissues such as intestines, with a main working principle being to sever and anastomose tissues by means of a knife and staples.

A current surgical stapler mainly has functions of cutting and anastomosis. During clinical use, it is found that the existing stapler mainly has the following three defects: 1. At an anastomotic part, tissue proliferation may occur during human body repair. The tissue proliferation is uncontrollable, and may be outward or inward, and inward proliferation may lead to narrowing or even blockage of a lumen again. 2. Liquid leakage may occur at the anastomotic part due to the anastomosis being not in place, and may lead to inflammation and other complications in other parts of the human body. 3. During cutting-off, transmission nerves in the intestine or other tissues in the body are also cut off. As a result, a system of this part may be disordered and cannot operate normally. For example, movement of a normal intestine may drive substances in the intestine to move downward, but a disordered system may cause the substances in the intestine to surge upward, resulting in a postoperative adverse reaction and even losing a part of functions.

SUMMARY

An objective of the present disclosure is to provide a surgical stapler to solve the disadvantages of existing staplers.

The technical solutions used by the present disclosure to solve the technical problems are as follows: A surgical stapler includes an anvil and a cartridge that cooperate with each other, a handle, and a connecting tube for connecting the cartridge to the handle. A stent for distracting an orifice is movably connected to a front end of the anvil, and the stent has a flexible and deformable tubular structure and can distract a lumen of the human orifice after a radial constraint is removed.

In order to prevent leakage at an anastomotic part, the stent is coated with an anti-leakage film.

In order to solve the problem that a functional loss of the anastomotic part after surgery may lead to substance reflux, an anti-reflux film is further arranged on the stent.

In order to facilitate binding and untie the stent during surgery, a stent mounting rod is arranged at the front end of the anvil, the stent is sleeved on the stent mounting rod, and a binding wire for binding the stent to the stent mounting rod is in slipknot connection to the stent.

In order to facilitate operation and loosening of the stent, an end of the binding wire at which a slipknot can be opened penetrates the anvil, a release wire in butt joint with the binding wire is arranged on the handle, and the release wire penetrates the connecting tube and the cartridge, with an end extending out of the cartridge.

Further, a take-up wheel is arranged on the handle, and an end of the release wire is wound around the take-up wheel.

In order to avoid blocking of the release wire during take-up, a wire tube is further arranged, and the wire tube extends from the handle to an end of the cartridge.

The present disclosure has the following beneficial effects. The present disclosure is improved based on an existing surgical stapler. Against the problem of lumen narrowing and blockage caused by tissue proliferation after anastomosis by the surgical stapler, a detachable stent is added at a front end of the stapler, and after anastomosis surgery, the stent is used to distract a lumen of a human orifice, so that a tissue can be effectively inhibited from proliferating toward the lumen of the human orifice during healing of an anastomotic part. An anti-leakage film is additionally arranged on the stent, and the anti-leakage film is distracted with the stent and attached to an inner wall of the orifice, thereby solving the problem of liquid leakage caused by the anastomosis being not in place. The anti-reflux film can make substances in the orifice transfer in one direction, but fail to flow in a reverse direction, thus solving the problem that substance reflux occurs at the anastomotic part after the surgery due to a function loss. For the stent, a stent mounting rod is added to the stapler, and a method of slipknot binding by a binding wire is used, so that the stent can be quickly separated from the stapler after the surgery by pulling a slipknot, and the stent is left in the orifice. The binding wire is pulled by means of a release wire, which is simple in structure, enables a fast operation during surgery, and is less likely to cause an error. In addition, the release wire is driven by means of a take-up wheel, which enables a simpler and more convenient operation.

BRIEF DESCRIPTION OF THE DRAWINGS

The present disclosure will be described in detail below with reference to the accompanying drawings and embodiments.

DETAILED DESCRIPTION OF THE EMBODIMENTS

Figure 1:
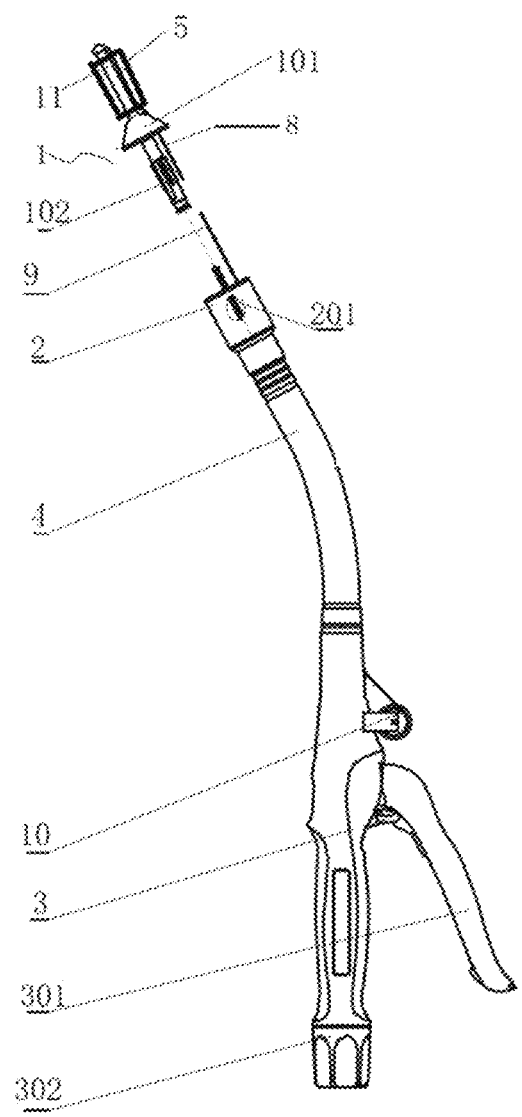
FIG. 1 is a schematic diagram of a three-dimensional structure according to the present disclosure.
Figure 2:
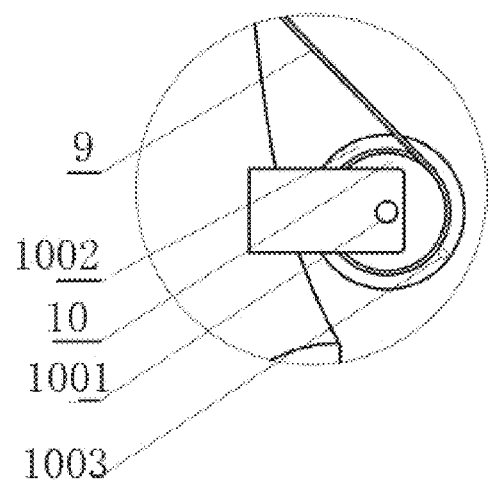
FIG. 2 is a partial schematic diagram of a take-up wheel according to the present disclosure.

Embodiment 1: As shown in FIG. 1 and FIG. 2, a surgical stapler includes anvil 1 and cartridge 2 that cooperate with each other to implement anastomosis of a cut-off part of an orifice, and further includes handle 3 and connecting tube 4 for connecting the cartridge 2 to the handle 3. As a common structure of the surgical stapler, the anvil 1 includes anvil plate 101 and anti-rotation and anti-slip socket 102. The anvil plate 101 has a conical or round-headed structure. Anti-rotation and anti-slip insert 201 that is inserted in and fitted with the anti-rotation and anti-slip socket 102 is arranged in the cartridge 2. The handle 3 is a hand-held operating component, including anastomosis wrench 301 and adjusting knob 302 for controlling the anti-rotation and anti-slip insert 201 to extend or retract. The above structures are all operating structures of an existing stapler, and a cooperation relationship therebetween is not explained in detail herein.

In order to solve the problem that in an existing stapler, after surgery, a tissue at an anastomotic part of the orifice proliferates toward an interior of the orifice, thereby causing the orifice to be narrowed or even blocked, stent 5 for distracting the orifice is movably connected to a front end of the anvil 1. The stent 5 has a flexible and deformable tubular structure, and can distract a lumen of the human orifice after a radial constraint is removed. The orifice mentioned in the present disclosure mainly refers to an esophagus, an intestine, or the like. An existing stent for distracting the orifice may be used as the stent 5. For example, a Chinese patent No. 201280027216.6, entitled "ESOPHAGEAL STENT", discloses a stent structure for distracting an orifice. After anastomosis surgery is completed, the stent 5 is supported at the anastomotic part, thus effectively solving the problem of inward tissue proliferation after the anastomosis surgery is completed.

In order to facilitate mounting and release of the stent 5, according to the present disclosure, stent mounting rod 11 is further added at the front end of the anvil 1. The stent 5 is sleeved on the stent mounting rod 11, and the stent 5 is bound and fixed to the stent mounting rod 11 by means of binding wire 8. The binding wire 8 implements fixed connection by fastening a slipknot. A free end of the binding wire 8 at which the slipknot can be opened penetrates the anvil plate 101 on the anvil 1, and a hole for the binding wire 8 to pass through is provided in the anvil plate 101. Release wire 9 in butt joint with the binding wire 8 is arranged on the handle 3, and the release wire 9 penetrates the connecting tube 4 and the cartridge 2, with an end extending out of the cartridge 2. When anastomosis surgery is performed, a surgeon places the anvil 1 into a to-be-anastomosed orifice before performing an orifice anastomosis operation, and the anti-rotation and anti-slip socket 102 and the free end of the binding wire 8 are exposed outside an orifice opening, and the orifice opening is stitched into a purse. Then a fistula is made on a wall of another to-be-anastomosed orifice. The anti-rotation and anti-slip socket 102 and the cartridge 2 pass through the fistula, and the anti-rotation and anti-slip insert 201 and the end of the release wire 9 exceed the orifice opening. The orifice opening is also stitched into a purse. Then the free end of the binding wire 8 and the end of the release wire 9 are in butt joint and knotted together. The anti-rotation and anti-slip insert 201 is inserted into the anti-rotation and anti-slip socket 102, and the adjusting knob 302 is rotated, so that the two to-be-anastomosed orifice openings lean together. Take-up wheel 10 is rotated to straighten the binding wire 8 and the release wire 9 naturally. The anastomosis wrench 301 is pressed to anastomose the two orifice openings (staples in the cartridge staple the two orifices together), the stapler is rotated gently in a small range. The stapler is retracted by about half the length of the stent 5, and the take-up wheel 10 is rotated to release the stent 5 at an anastomosis opening. The stapler is removed, and the artificial fistula is stitched to complete the anastomosis.

To facilitate operation of the release wire 9, the take-up wheel 10 is arranged on the handle 3, and an end of the release wire 9 is wound around the take-up wheel 10. The take-up wheel 10 is mounted on the handle 3 by means of rotating shaft 1001, and hand wheel 1002 is further mounted on the rotating shaft 1001. Handle lever 1003 is arranged on the hand wheel 1002, and the take-up wheel 10 is driven to rotate by rotating the hand wheel 1002, so as to pull and take up the release wire 9. The structure is simple and convenient to operate. In order to prevent the release wire 9 from interfering with other structures in the handle 3 and the connecting tube 4 and affecting take-up, a wire tube (not marked in the figure) is further provided. The wire tube extends from an interior of the handle 3 to an end of the cartridge 2. The handle 3 is provided with a through hole for the release wire 9 to pass through, and the release wire 9 passes through the through hole from the take-up wheel 10 and then enters the wire tube, so that the wire tube can ensure that the release wire 9 is not affected by other structures, thereby improving operation reliability.

Figure 3:
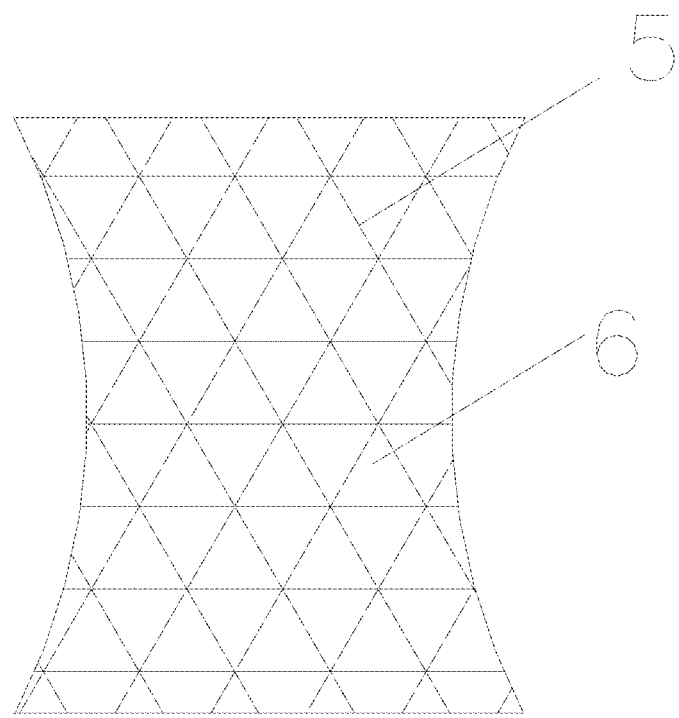
FIG. 3 is a schematic structural diagram of a stent with an anti-leakage film according to the present disclosure.

Embodiment 2: As shown in FIG. 1 to FIG. 3, a surgical stapler includes anvil 1 and cartridge 2 that cooperate with each other to implement anastomosis of a cut-off part of an orifice, and further includes handle 3 and connecting tube 4 for connecting the cartridge 2 to the handle 3. As a common structure of the surgical stapler, the anvil 1 includes anvil plate 101 and anti-rotation and anti-slip socket 102. The anvil plate 101 has a conical or round-headed structure. Anti-rotation and anti-slip insert 201 that is inserted in and fitted with the anti-rotation and anti-slip socket 102 is arranged in the cartridge 2. In order to solve the problems that in an existing stapler, after surgery, a tissue at an anastomotic part of the orifice proliferates toward an interior of the orifice and an improper surgery causes a liquid in the orifice to flow out of the anastomotic part, stent 5 for distracting the orifice is movably connected to a front end of the anvil 1, and the stent 5 is coated with anti-leakage film 6. After the surgery is completed, the stent 5 and the anti-leakage film 6 are supported on an inner wall of the orifice, thus effectively solving the problem of inward orifice tissue proliferation and liquid leakage at the anastomotic part. A structure of the anti-leakage film 6 is attached to the stent 5, and an existing film-coated stent structure may be adopted. For example, a Chinese patent No. 022192514, entitled "RECOVERABLE ESOPHAGEAL AND TRACHEAL STENT", discloses a film-coated stent structure, or of course, other film-coated stent structures may be adopted. Other aspects are the same as those of Embodiments 1.

Figure 4:
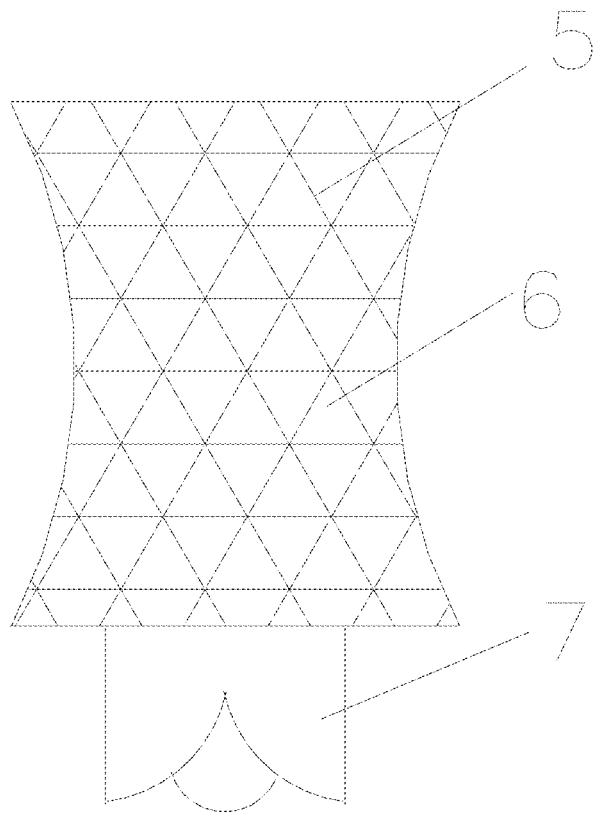
FIG. 4 is a schematic structural diagram of a stent with an anti-reflux film according to the present disclosure.

As shown in FIG. 1, FIG. 2, and FIG. 4, a surgical stapler includes anvil 1 and cartridge 2 that cooperate with each other to implement anastomosis of a cut-off part of an orifice, and further includes handle 3 and connecting tube 4 for connecting the cartridge 2 to the handle 3. As a common structure of the surgical stapler, the anvil 1 includes anvil plate 101 and anti-rotation and anti-slip socket 102. The anvil plate 101 has a conical or round-headed structure. Anti-rotation and anti-slip insert 201 that is inserted in and fitted with the anti-rotation and anti-slip socket 102 is arranged in the cartridge 2. In order to solve the problems that in an existing stapler, after surgery, a tissue at an anastomotic part of the orifice proliferates toward an interior of the orifice, an improper surgery causes a liquid in the orifice to flow out of the anastomotic part, and substance reflux occurs in the orifice, stent 5 for distracting the orifice is movably connected to a front end of the anvil 1, and the stent 5 is coated with anti-leakage film 6. In addition, anti-reflux film 7 is further arranged on the stent 5. An existing anti-reflux membrane structure design, such as an anti-reflux flap and a membranous skirt structure involved in a Chinese patent No. 981114075 entitled "ARTIFICIAL CARDIA", is adopted for the structure of the anti-leakage film 6. After the surgery is completed, the stent 5 and the anti-leakage film 6 are supported on an inner wall of the orifice, thus effectively solving the problem of inward orifice tissue proliferation and liquid leakage at the anastomotic part. In addition, the anti-reflux film 7 can achieve a very good anti-reflux effect. Other aspects are the same as those of Embodiments 2.

The present disclosure has been described above by way of example with reference to the accompanying drawings. Obviously, the specific implementation of the present disclosure is not limit by the above-mentioned way. Various immaterial improvements performed by means of the method concepts and technical solutions of the present disclosure or direct application of the above concepts and technical solutions of the present disclosure to other occasions without improvements shall fall within the protection scope of the present disclosure.

What is claimed is:

1. A surgical stapler, comprising an anvil and a cartridge that cooperate with each other, a handle, and a connecting tube for connecting the cartridge to the handle, wherein a stent for widening an orifice is movably connected to a front end of the anvil, and the stent has a flexible and deformable tubular structure and is configured to be separated from a stapler body after a radial constraint is removed and to widen a lumen of the human orifice, wherein a stent mounting rod is arranged at the front end of the anvil, the stent is sleeved on the stent mounting rod, and a binding wire for binding the stent to the stent mounting rod is in slipknot connection to the stent.

2. The surgical stapler according to claim 1, wherein the stent is coated with an anti-leakage film.

3. The surgical stapler according to claim 2, wherein an anti-reflux film is further arranged on the stent.

4. The surgical stapler according to claim 1, wherein an anti-reflux film is further arranged on the stent.

5. The surgical stapler according to claim 1, wherein an end of the binding wire where a slipknot is configured to be opened penetrates the anvil, a release wire in butt joint with the binding wire is arranged on the handle, and the release wire penetrates the connecting tube and the cartridge, with an end extending out of the cartridge.

6. The surgical stapler according to claim 5, wherein a take-up wheel is arranged on the handle, and an end of the release wire is wound around the take-up wheel.

7. The surgical stapler according to claim 5, further comprising a wiring tube, wherein the wiring tube extends from an interior of the handle to an end of the cartridge.

* * * * *